United States Patent [19]
Farrell

[11] Patent Number: 5,370,674
[45] Date of Patent: Dec. 6, 1994

[54] METHOD OF HEATING MEDICAL LIQUIDS

[76] Inventor: Harriet M. Farrell, 2319 Worden St., San Diego, Calif. 92107

[21] Appl. No.: 35,299

[22] Filed: Mar. 22, 1993

[51] Int. Cl.$^5$ .............................. A61F 7/06; A61F 7/12
[52] U.S. Cl. ..................................... 607/96; 607/112; 607/113; 604/113
[58] Field of Search ............... 128/400, 403, DIG. 12; 604/113, 408; 607/96, 113

[56] References Cited

U.S. PATENT DOCUMENTS

| | | | |
|---|---|---|---|
| 4,756,311 | 7/1988 | Francis, Jr. ......................... | 128/403 |
| 4,804,367 | 2/1989 | Smith et al. ......................... | 604/113 |
| 4,934,336 | 6/1990 | White ..................... | 128/DIG. 12 X |
| 4,953,550 | 9/1990 | Dunshee ............................. | 128/403 |

OTHER PUBLICATIONS

Anon., "Hypothermia Predicts Postoperative Ischemia and Morbidity", *Convetnion Reporter*, 22, 2, 9 (1992) [1992 Meeting: Amer. Soc'y. of Anesthesiologists].
Bostek, *AANA Journal*, 60, 6, 561–566 (Dec. 1992).
Bowen, *AANA Journal*, 60, 4, 369–373 (Aug., 1992).
Carolon Company: "Champ Hotwrap" advertising brochure, 2 pages (date unknown).
Mellan, *Polyhydric Alcohols*, pp. 46–71 (1962).
Monick, *Alcohols: Their Chemistry, Properties and Manufacture*, pp. 277–364 [Ch.4] (1968).

*Primary Examiner*—Richard J. Apley
*Assistant Examiner*—Beverly A. Meindl
*Attorney, Agent, or Firm*—Brown, Martin, Haller & McClain

[57] ABSTRACT

A simple and cost-effective method is disclosed to avoid hypothermia and other adverse effects of administration of chilled fluids such intravenous medicating fluid, an intravenous hydrating fluid or blood to a patient during medical procedures such surgery and post-operative recovery. The method provides heat to such fluids, using an elasticized heating device such that each unit can be quickly and easily replaced with another unit when the heating effect of the first significantly diminished, so that the fluid administered is kept at the desirable administration temperature during the entire surgical procedure. The method involves providing a conduit through which the fluid is administered to the patient (usually intravenously or subcutaneously), providing the elasticized device incorporating a semi-solid composition with a relatively high heat capacity, preheating the composition to administration temperature; wrapping the device around a length of the conduit; and retaining the device in place by quick release fasteners, so that the pre-heated composition heating the fluid passing through the conduit to the desired temperature immediately prior to administration of the fluid to the patient. Use of two or more devices simultaneously is also disclosed. Further, as the heat content of one device is depleted, the method also includes quick replacement of that device with another, previously preheated, so that the heating of the fluid continues substantially continuously at the desire temperature.

12 Claims, 1 Drawing Sheet

METHOD OF HEATING MEDICAL LIQUIDS

BACKGROUND OF THE INVENTION

1. Field of the Invention

The invention herein relates to medical administration of liquids such as intravenous fluids and transfused blood. More particularly it relates to methods of maintaining a desired temperature of such fluids.

2. Description of the Prior Art

In many medical procedures and situations, it is necessary to administer fluids or liquids of one type or another to a patient. Typically a patient will be given one or more types of liquid medication or hydrating liquids through intravenous administration. Similarly, patients are often provided with transfused blood intravenously. Typical of the types of medical procedures or situations in which fluids are administered include during surgery, in treatment of cardiac arrest, in nurseries, during administration of blood from blood banks, to burn patients and during post-operative recovery.

It is well known that such liquids or fluids should not be at low temperatures when administered to the patients, since the temperature differential between the fluid's temperature and the patient's body temperature can have serious adverse effects upon the patient who is already in a weakened condition. For instance, when chilled a patient's circulatory system has less capacity to carry oxygen. The problem of chilling from cold fluids is particularly acute for patients during surgery, when a patient's system is already subject to the trauma of surgery and is also suppressed by the anesthetic, or during treatment for cardiac arrest. See, e.g., Bowen, *J. Amer. Assoc. Nurse Anesths.*, 60, 4, 369–373 (1992); Bostek, *J. Amer. Assoc. Nurse Anesths.*, 60, 6, 561–566 (1992); and Anon., *Convention Reporter*, 22, 2, 9 (Dec. 1992) [Meeting of Amer. Society of Anesthesiologists (Oct. 1992)].

Unfortunately, however, it is often difficult to deliver fluid to the patient at the appropriate temperature. Many fluids are held in refrigerated storage until just prior to administration to the patient. In addition, it is common practice for operating rooms and recovery rooms to be vigorously air conditioned or to use laminar air flow, both of which keep the ambient temperature quite low. While there are sound medical reasons for this practice, including the comfort of the surgical team during lengthy surgical procedures and inhibition of infection in the patient, it means that the fluids on hand in the operating room or recovery room will remain at lowered temperatures.

Since it has been recognized that hypothermia of surgical patients is a serious problem, and that use of chilled intravenous or transfused fluids will aggravate that condition and cause further cooling of internal organs, there have been numerous attempts in the past to provide techniques and equipment for heating such fluids prior to administration to the patient. The Bostek and Bowen articles mentioned above describe typical examples. Overall, these various devices have not proved uniformly successful. Stand-alone continuous electric heaters through which the fluids are passed tend to be cumbersome and must be positioned close to the patient, and are thus frequently in the way of the surgical team in what is already normally a very crowded area surrounding the operating table. They also require electrical power cords, and such cords interfere with the surgical team's movements and can be dangerous. In addition, they are costly to purchase and operate. Their use is, therefore, frequently avoided.

Alternatively, there have been efforts to use small tube-like devices which can be preheated and through which the fluid is flowed prior to administration to the patient. Such devices have had shortcomings. Being small, they rapidly cool and after a short time no longer heat the fluid effectively. Further, such devices have been difficult and time consuming to disengage from the fluid flow lines. The result has been that after an initial period of adequate heating, the fluid subsequently administered to the patient is once again in a chilled condition, since the surgical team members do not have the time to engage in lengthy disassembly, reheating and replacement of these devices.

Since the problem of hypothermia in patients and the aggravating effects of administration of chilled fluids is an on-going problem, it would therefore be advantageous to have a simple method for providing heat to these fluids, using a device of a sufficiently simple design that each unit could be quickly and easily replaced with another heated unit when the heating effect of the first significantly diminished. The fluids administered to the patients would therefore be kept substantially uniformly at the desirable administration temperature during the entire surgical procedure.

SUMMARY OF THE INVENTION

The method of this invention is a quick and simple method for providing continuous heating of medical fluids which are administered to patients, particularly for patients undergoing intravenous fluid administration during surgery and/or post-operative recovery. The devices used in this invention are themselves simple and readily available. Equally important, the method by which these devices are used provides for very quick combination of the fluid supply line and the heating device, and equally quick and simple replacement of a freshly-heated device for one which has had its heat storage depleted. Further, it is a highly cost-effective way to provide for heating of the fluids, particularly as compared to the elaborate electrical machines described above.

In its broadest form, the invention herein is a method of heating fluids to a temperature appropriate for administration to a patient which comprises providing a fluid supply conduit through which the fluid is passed to be administered to the patient, preferably via intravenous or other subcutaneous administration, providing an elasticized device, normally elongated, having an interior containing a semi-solid composition having a relatively high heat capacity, pre-heating the composition within the elasticized device to a pre-determined desired administration temperature; wrapping the device around a predetermined length of the fluid conduit; and retaining the device in place by quick release fastening means; such that the pre-heated composition with the device transfers heat to the adjacent conduit thereby heating the fluid passing through the conduit to the desired temperature immediately prior to administration of the fluid to the patient.

In a further embodiment, the method includes rapidly disengaging the quick-release fastener, separating a device from which a significant quantity of the heat of its composition has been transferred, providing an equivalent device with its included composition preheated to the desired temperature, and quickly attaching the second device to the fluid conduit using quick-release fastening means, such that the heating of the conveyed fluid prior to administration to the patient continues substantially continuously at the desire temperature.

In yet another embodiments, a second device is heated and attached to the fluid conduit prior to removal of a previously attached device which has transferred a significant amount of its heat, and the previously attached device is then removed, further such that the heating of the conveyed fluid prior to administration to the patient continues substantially continuously at the desire temperature.

DETAILED DESCRIPTION AND PREFERRED EMBODIMENTS

Figure 1:
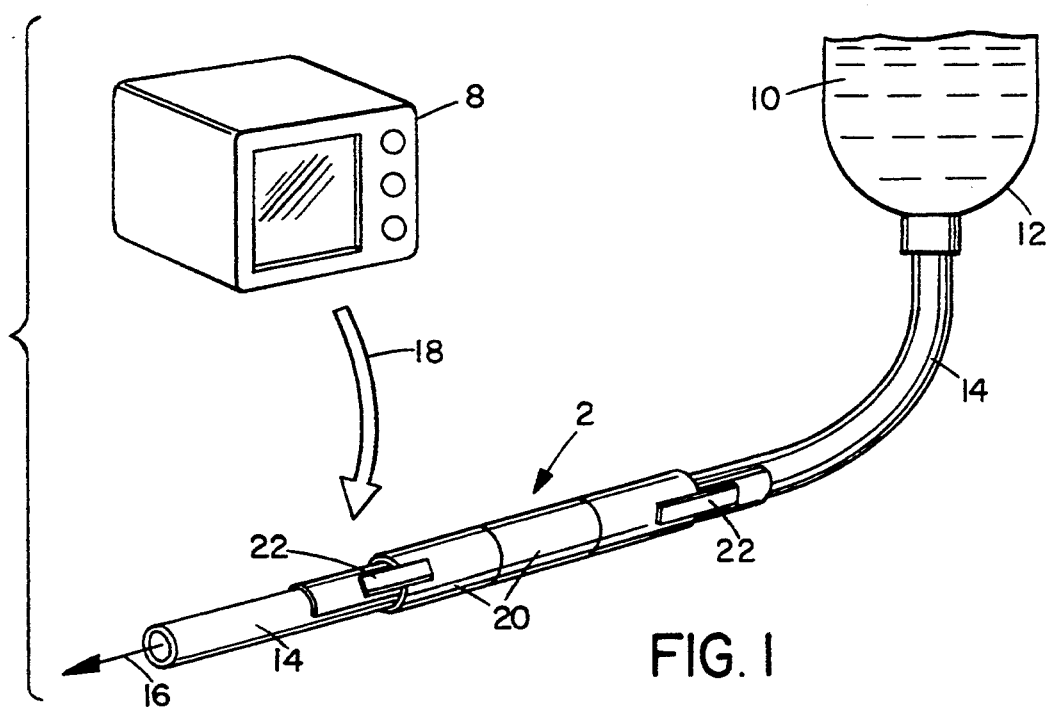
FIG. 1 is a schematic view illustrating the method of heating of the fluid as defined in this invention.

The process of this invention will be best understood by reference to the drawings. In FIG. 1 an elongated elasticized heating device 2 is shown, which has the general appearance of an elastic bandage, has enclosed within itself one or more pockets 4 each containing a semi-solid composition 6 with a high heat capacity. Both the device 2 and the composition 6 will be described below in further detail. Prior to use the heating device 2 is pre-heated, for instance by use of a microwave heater 8, so that the semi-solid composition 6 will be heated to the desired pre-heat temperature from which it in turn can transfer heat to the fluid 10 which is to be administered to the patient. The fluid 10 is contained in a suitable reservoir such as an IV bottle 12 from which it is conveyed to the patient (not shown) through tubing or a similar flexible conduit 14 as indicated by the arrow 16.

Once the composition 6 has reached the desired pre-heat temperature, the device 2 is transferred from the heater 8 as indicated by arrow 18, stretched moderately to activate the elasticity in the device 2 and wrapped in abutting or overlapping coils 20 around the outside of an extended length of tubing 14. Each end of the wrapped elasticized heating device 2 is then secured to the next adjacent coil 20 through a quick-release fastener 22. The device 2 is thus placed and retained quickly and easily; it can then transfer the heat contained in the composition 6 directly through the wall of conduit 14 to the fluid 10 passing through such that upon administration to the patient, the fluid 10 is at the appropriate administration temperature.

After a device 2 has been in place on the tubing 14 for some time, it will of course begin to cool as its heat is transferred to the fluid 10. In order to maintain the fluid 10 in the desired temperature range on a continual basis throughout the medical procedure, it is contemplated that as a first device 2 begins to cool, it will be removed from the tubing 14 and replaced by a second pre-heated device, and that when it cools by a third device, and so forth as long as needed or desired. In some cases, as where the length of tubing available for wrapping with the device 2 is relatively short, the first device will be fully removed before the second device is attached. Alternatively, and preferred where there is a sufficiently long section of tubing 14, one can put the second device 2 in place prior to removal of the cooling first device 2, and thus minimize any change in fluid administration temperature. One may establish a replacement and reheating schedule for individual devices 2 so that there are always two or more devices 2 in place along a section of tubing 14 and an essentially constant administration temperature of the fluid is maintained.

The length of the portion of tubing 14 which is to be surrounded by the device 2 will depend on a number of factors. These will include the inlet temperature and the desired administration temperature of the fluid 10, the diameter and wall thickness of the tubing 14, the thickness of the device 2, the rate of flow of the fluid 10 through the tubing 14 and the length of the device 2 that can be easily handled, wrapped quickly and securely and then subsequently unwrapped by surgical team personnel.

Normally the length of the device 2 and degree of pre-heating of the composition 6 will be chosen so that the administration temperature of the fluid 10 to the patient closely approximates normal body temperature, i.e., 37°-38° C. Given the flow rate of the fluid, the known temperature of the fluid in the reservoir and the size of the tubing 14, it is then a simple matter for one skilled in the art to readily determine the required degree of heating of the composition 6 and the length of wrapping of the device 2 around the conduit 14. Commonly a length of about 6-24 inches (15-60 cm) of the tubing 14 will be wrapped and exposed to the heat from the device 2, and the composition will be preheated to a temperature of about 40°-45° C. Heating of the composition in a conventional microwave oven at full power will normally take about 60-90 seconds to bring the composition from ambient temperature to the appropriate heating temperature.

Figure 3:
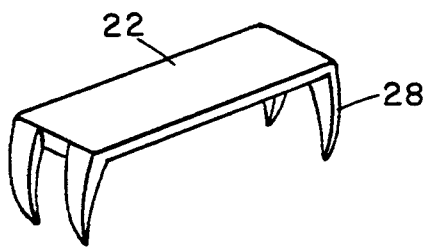
FIG. 3 is a pictorial view of a typical quick-release fastener.
Figure 4:
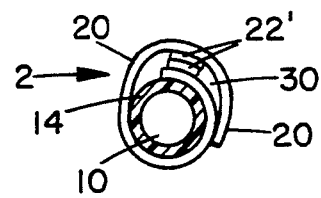
FIG. 4 is a cross-sectional view of a fluid conduit with a heating device wrapped around it, showing in exaggerated form one alternative means of securing the heating device in place.

There are a number of ways of securing the ends of the device 2 to hold it in place on the tubing 14. Typically, the fastening device 22 can be a toothed clip as shown in FIG. 3, where the curved prongs 28 hook into the elasticized fabric 30 of the device 2 and are then readily unhooked when the device 2 is to be removed from the tubing. Such clips are conventionally used with elastic bandages and are readily obtainable commercially. Alternatively and preferably, as shown in FIG. 4, one can attach to opposite sides of the fabric 30 short pieces of hook-and-loop fastener material 22' (such as that sold commercially under the tradename "Velcro"). Thus, when the coils 20 of the device 2 are wrapped around the tubing 14, the pieces of hook-and-loop fastener 22' will engage each other, thus securing the ends of the device 2 in position. When it is desired to unwrap the device 2 and remove it, that can be simply accomplished by pulling the two parts of the hook-and-loop fastener 22' apart.

Figure 2:
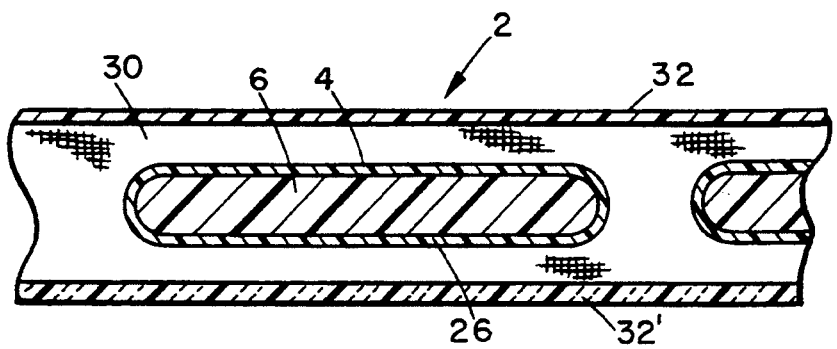
FIG. 2 is a partial axial sectional view of a typical heating device useful in this invention.

The structure of the device 2 is most easily understood from FIG. 2. The device is primarily made from an elasticized woven fabric 30 typical of the fabrics from which conventional elastic bandages are made. Embedded within the fabric 30 are one or more pockets 4 containing the heatable composition 6. The composition is normally a "semi-solid" material, which for the purposes of this invention will be considered to be any material which has the consistency, flexibility and thixotropic properties of materials commonly referred to as "gels" or "slushes," and which has a reasonably high heat capacity sufficient to retain and emit significant quantities of heat over a prolonged period. There are a number of materials known for this purpose, some of which are commercially available. Typically they are water-based materials containing significant quantities of dihydric alcohols, commonly propylene glycol. The water content will normally be on the order of about 60–90 percent by weight of the composition, with most of the balance being the dihydric alcohol. The composition may also contain various small quantities of stabilizers, dyes, biocides and the like. Typical compositions are illustrated in a number of publications including Dunshee, U.S. Pat. No. 4,953,550 (1990); Mellan, *Polyhydric Alcohols* (1962), especially pages 46–71, and Monick, *Alcohols: Their Chemistry, Properties and Manufacture* (1968), especially Chapter 4. Those skilled in the art will immediately recognize other compositions, in addition to the water/dihydric alcohol compositions, which will have the desired properties described and which will be usable in this invention. Preferably the materials used in composition 6 will be non-toxic, non-corrosive and otherwise inert or harmless, so that they will not degrade the device 2 and, if a leak should develop, they will not harm the patient, medical personnel or equipment.

It will also be recognized that both the composition 6 and the fabric 30 must be such that they are not harmed or degraded by heating in the heating device 8. The composition 6 must also be such that heating to the desired temperature does not generate any significant amount of gas or vapor which would cause the pocket 4 to be ruptured or otherwise cause any of the composition 6 to leak. Depending on the degree of solidity of the composition 6 and the nature of the fabric 30 one may optionally also include a liner or pouch 26 surrounding the composition 6 between the composition 6 and the fabric 30. Typical materials and configurations are shown in the Dunshee patent mentioned above. It may be desirable to have the entire fabric 30 covered with an outer protective layer 22 (only a portion of which is shown). Layer 32 could be mace of an elasticized canvas material with a plastic material incorporated therein, to resist the accumulation of dirt or grime because of repeated handling or of being thrown aside during the haste which necessarily accompanies many medical procedures, and which also permits ready cleaning of the surface.

In addition, one may wish to have an layer of insulating material 32' placed on the exterior of the device 2 on the side which will be opposite the surface which is to contact the conduit 14, in order to help retain heat within composition 6 and to avoid loss of heat to the ambient surroundings. Such will be feasible, however, only if such an insulating layer has sufficient flexibility and elasticity to be stretched and secured as required for securing device 2 in the present method.

A typical device 2 which can be used in the process of this invention is one sold commercially under the tradename "Champ Hot Wrap" by Carolon Company of Winston-Salem, N.C.

It will be evident to those skilled in the art that there are a number of embodiments of this invention which, while not expressly set forth above, are clearly within the scope and spirit of the invention. The above description is therefore intended to be exemplary only, and the scope of the invention is to be limited solely by the appended claims.

I claim:

1. A method of heating a fluid to a temperature appropriate for administration to a patient while said fluid is being transferred from a fluid reservoir to said patient, which comprises:
   a. providing a fluid supply conduit through which said fluid is passed from said reservoir to be administered to said patient;
   b. providing a first elasticized device comprising an elongated flexible elasticized band having incorporated therein at least one internal chamber in which is disposed a semi-solid heat-absorbing and -emitting composition having a relatively high heat capacity;
   c. pre-heating said composition within said elasticized device to a predetermined desired temperature;
   d. wrapping said device around a predetermined length of said conduit; and
   e. retaining said device in place by quick release fastening means;
   such that said pre-heated composition within said device transfers heat to said adjacent conduit thereby heating said fluid passing through said conduit from said reservoir to said administration temperature immediately prior to administration of said fluid to said patient.

2. A method as in claim 1 wherein said fluid is an intravenous medicating fluid, an intravenous hydrating fluid or blood.

3. A method as in claim 2 wherein said administration temperature is substantially equivalent to human body temperature.

4. A method as in claim 3 wherein said administration temperature is in the range of 37°–38° C.

5. A method as in claim 1 wherein said composition comprises a semi-solid material having consistency, flexibility and thixotropic properties equivalent to a gel or slush.

6. A method as in claim 5 wherein said material comprises water and a polyhydric alcohol.

7. A method as in claim 1 wherein said band comprises elastic bandage material.

8. A method as in claim 7 where said band further comprises an exterior layer which resists becoming soiled and which is readily cleaned.

9. A method as in claim 1 further comprising:
   f. providing a second elasticized device substantially like said first elasticized device with an equivalent composition therein;
   g. pre-heating said composition within said second elasticized device to an equivalent pre-determined desired temperature;
   h. removing said first device by disengaging said quick release fastening means; and
   i. replacing said first device with said second device in said wrapped position around said length of said conduit and retaining said second device in place by said quick release fastening means;
   such that said pre-heated composition within second said device thereupon transfers heat to said adjacent conduit thereby continuing heating said fluid passing through said conduit to said administration temperature immediately prior to administration of said fluid to said patient.

10. A method as in claim 1 further comprising:
   f. providing a second elasticized device substantially like said first elasticized device with an equivalent composition therein;

g. pre-heating said composition within said second elasticized device to an equivalent pre-determined desired temperature;

h. placing said second device a wrapped position around said length of said conduit adjacent to said first device and retaining said second device in place by said quick release fastening means; and i. after a period of time removing said first device by disengaging said quick release fastening means;

such that said pre-heated compositions within both said first and said second devices transfer heat simultaneously to said adjacent conduit thereby preventing any disruption in heating of said fluid passing through said conduit to said administration temperature immediately prior to administration of said fluid to said patient.

11. A method as in claim 9 wherein said first and second elasticized devices are repeatedly interchanged, with one device being reheated to said desired temperature while the other device is in place on said conduit.

12. A method as in claim 10 wherein said first and second elasticized devices are repeatedly interchanged, with one device being reheated to said desired temperature while the other device is in place on said conduit.

* * * * *